United States Patent
Cochet et al.

(10) Patent No.: US 8,686,144 B2
(45) Date of Patent: Apr. 1, 2014

(54) CONDENSED PYRIDINE DERIVATIVES USEFUL AS POTENT INHIBITORS OF THE PROTEIN KINASE CK2

(75) Inventors: Claude Cochet, Claix (FR); Renaud Prudent, Saint-Egreve (FR); Virginie Moucadel, Saint-Egreve (FR); Chi-Hung N'guyen, Antony (FR)

(73) Assignees: Commissariat a l'Energie Atomique et aux Energie Alternative, Paris (FR); Institut National de la Sante et de la Recherche Medicale (INSERM), Paris (FR); Institut Curie, Paris (FR); Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 13/387,912

(22) PCT Filed: Jul. 28, 2010

(86) PCT No.: PCT/IB2010/002157
§ 371 (c)(1),
(2), (4) Date: Mar. 23, 2012

(87) PCT Pub. No.: WO2011/013002
PCT Pub. Date: Feb. 3, 2011

(65) Prior Publication Data
US 2012/0178759 A1    Jul. 12, 2012

(30) Foreign Application Priority Data
Jul. 28, 2009  (EP) .................................... 09290595

(51) Int. Cl.
*C07D 471/04* (2006.01)

(52) U.S. Cl.
USPC ........................................... 544/344; 546/70

(58) Field of Classification Search
None
See application file for complete search history.

(56) References Cited

U.S. PATENT DOCUMENTS

| 5,091,388 A | 2/1992 | Bisagni et al. |
| 2004/0229895 A1 | 11/2004 | Jagtap et al. |
| 2007/0249653 A1 | 10/2007 | Jagtap et al. |

FOREIGN PATENT DOCUMENTS

| EP | 0 402 232 | 12/1990 |
| FR | 2 327 783 | 5/1977 |
| WO | WO 2009/054401 A1 * | 4/2009 |

OTHER PUBLICATIONS

Vinogradov et al., 14(1) Bioconjugate Chem., 120-135 (2003).*
Berge et al., Pharmaceutical Salts, 66(1) J. Pharma. Sci. 1-19 (1977).*
Hoang, T.M. et al., "Benzo[e]pyridoindoles, novel inhibitors of the aurora kinases," Cell Cycle, Landes Bioscience, vol. 8, No. 5, pp. 765-772, (Mar. 1, 2009).
He, L., et al., "Design of antineoplastic agents based on the '2-phenylnaphthalene-type' structural pattern—synthesis and biological activity studies of 1 1H-indolo[3.2-c]quinoline derivatives," European Journal of Medicinal Chemistry, vol. 38, pp. 101-107,(2003).
Chen, Y., et al., "Synthesis and Cytotoxic Activity Evaluation of Indolo-, Pyrrolo-, and Benzofuro-Quinolin-2(1H)-Ones and 6-Anilinoindoloquinoline Derivatives," Bioorganic & Medicinal Chemistry, vol. 10, pp. 2705-2712, (2002).
Nguyen, C.H., et al., "Synthesis and Antitumor Activity of 1-[[(Dialkylamino)alkyl]amino]-4-methyl-5H-pyrido[4,3-b]benzo[e]-and -benzo[g])indoles. A New Class of Antineoplastic Agents," Journal of Medicinal Chemistry, vol. 33, pp. 1519-1528, (1990).
Wieczorek, J., et al., "Antineoplastic activity of azacarbazoles. III. Synthesis and antitumor evaluation of selected 2-, 3-aza and diaza analogs of carbazole," Archivum Immunologiae et Therapiae Experimentalis, vol. 34, No. 3, pp. 323-326 (1986) (English abstract only).
International Search Report issued Oct. 27, 2010 in PCT/IB10/02157 Filed Jul. 28, 2010.

* cited by examiner

*Primary Examiner* — Janet L Anders
*Assistant Examiner* — Timothy R Rozof
(74) *Attorney, Agent, or Firm* — Oblon, Spivak, McClelland, Maier & Neustadt, L.L.P.

(57) ABSTRACT

The invention relates to the use of specific compounds of formula (I) and their pharmaceutically-acceptable salts: (Formula 1) (I) as a new family of protein kinase CK2 inhibitors; the invention also relates to the use of compounds of formula (I) for the preparation of pharmaceutical compositions for the prevention and/or treatment of disorders and/or diseases chosen amongst cancers; autoimmune and inflammatory diseases; infectious diseases; diabetes angiogenesis related disorders; retinopathies and cardiac hypertrophy.

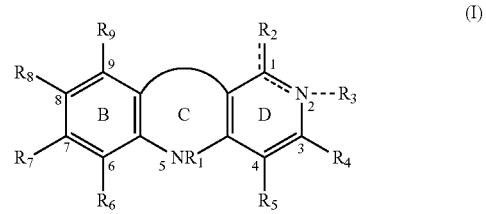

14 Claims, 4 Drawing Sheets

| U373 | DMSO | 1 | 2 |
|---|---|---|---|
| Sub-G1 | 3.26 ± 0.11 | 10.26 ± 0.36 | 11.59 ± 0.56 |
| G1 | 62.33 ± 1.28 | 53.84 ± 0.23 | 48.19 ± 0.48 |
| S | 15.82 ± 0.60 | 8.09 ± 0.10 | 12.62 ± 0.91 |
| G2/M | 19.02 ± 0.84 | 23.04 ± 0.07 | 27.70 ± 0.11 |

| HeLa | DMSO | 1 | 2 |
|---|---|---|---|
| Sub-G1 | 0.73 ± 0.06 | 0.74 ± 0.07 | 1.29 ± 0.3 |
| G1 | 56.14 ± 0.04 | 47.42 ± 0.41 | 43.15 ± 0.17 |
| S | 4.10 ± 0.11 | 5.94 ± 0.09 | 13.22 ± 0.29 |
| G2/M | 38.42 ± 0.2 | 44.76 ± 0.28 | 40.04 ± 0.36 |

CONDENSED PYRIDINE DERIVATIVES USEFUL AS POTENT INHIBITORS OF THE PROTEIN KINASE CK2

This application is a National Stage of PCT/IB10/002157 filed Jul. 28, 2010 and claims the benefit of EP 09290595.9 filed Jul. 28, 2009.

The invention relates to specific compounds of formula (I) and their pharmaceutically-acceptable salts as medicaments for inhibiting protein kinase CK2; the invention also relates to the use of compounds of formula (I) for the preparation of pharmaceutical compositions for the prevention and/or treatment of disorders and/or diseases chosen amongst cancers; autoimmune and inflammatory diseases; infectious diseases; diabetes and cardiac hypertrophy.

Figure 1:
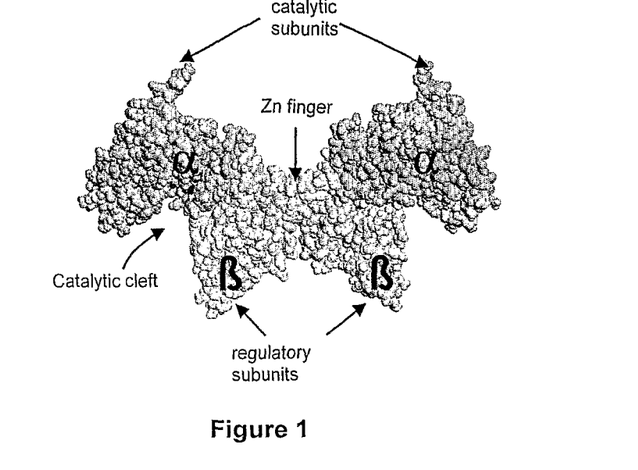
FIG. 1 shows a schematic representation of protein kinase CK2 comprising two α catalytic subunits and two β regulatory subunits.

The CK2 (or caseine kinase 2) protein is a multifunctional and ubiquitous serine/threonine kinase, very conserved in eukaryotes; this holoenzyme is composed of two catalytic subunits $\alpha$ and $\alpha'$ and two identical regulatory subunits $\beta$, associated in the form of $\alpha\alpha'\beta_2$, $\alpha'_2\beta_2$ or $\alpha_2\beta_2$ heterotetramers (see FIG. 1).

This protein plays an essential role in the control of many physiological or pathological processes; it is essential to embryonic development, to terminal differentiation, and to the control of progression of the cell cycle and of the cell survival; its expression is deregulated in many cancers including tumors of viral origin, where it contributes to the blocking of apoptosis (Ahmed et al., Trends in Cell Biology, 2002, 12, 226-230; Litchfield, Biochem. J., 2003, 369, 1-15); its dual function in promoting cell growth and in suppression of apoptosis may explain its oncogenic potential (Tawfic et al., Histol Histopathol., 2001 April; 16(2), 573-82).

The CK2 protein is also involved in inflammatory diseases like glomerulonephritis (Yamada et al., Proc. Natl. Acad. Sci., 2005, 102(21), 7736-7741); in some infectious diseases, like Human Immunodeficiency Virus (HIV), CytoMegaloVirus (CMV), Human Papillomavirus (HPV) and PolioVirus (PV), which exploit cellular CK2 to phosphorylate proteins which are essential to their life cycle; and in pathogenic parasite infections (Meggio et al., Biochemistry, 2004, 43, 12931-12936).

The recent association of aberrant CK2 expression with unfavourable prognostic markers in prostate cancers (Laramas et al., Eur. J. Cancer, 2007, 43, 928-934) and in acute myeloid leukemia (Kim et al., Clin. Cancer Res., 2007, 13, 1019-1028) confirms the implication of CK2 in tumour formation.

Because of its essential role in many physiological processes and because of the importance of the pathologies associated with its dysfunction, the CK2 protein represents a pharmacological target of interest for the development of medicinal products, in particular anticancer and antiviral agents.

The CK2 protein is therefore considered to be a relevant physiopathological target amenable to therapeutic intervention supporting the identification and the characterization of chemical inhibitors (Pagano et al., Biochem. Biophys. Res. Commun., 2004, 321, 1040-1044; Duncan et al., Biochimica et Biophysica Acta, 2008, 1784, 33-47).

As a number of diseases, like cancers, diabetes or inflammations, are linked to the perturbation of protein kinase CK2, there is a need of efficient inhibitors of this protein.

Several molecules have already been described in the prior art as being capable of inhibiting the CK2 protein:

ATP competitive inhibitors including four major molecules: Quercetine, Emodin, 4,5,6,7-tetrabromo-1H-benzotriazole (TBB) and its derivatives and 5-oxo-5,6-dihydroindolo-(1,2-a)quinazolin-7-yl)acetic acid (Duncan et al., Biochimica et Biophysica Acta, 2008, 1784, 33-47). Amongst these molecules capable of specifically inhibiting the catalytic activity of the CK2, mention may be made of TBB, a derivative of 5,6-dichloro-1-beta-D-ribofuranosylbenzimidazole (DRB), which shows a more marked selectivity towards CK2 (Sarno et al., FEBS lett., 2001, 496, 44-48; Duncan et al., Molecular and Cellular Proteomics, 2008, 7, 1077-1088). However, TBB and other kinase substrate analogs can inhibit the activity of other known or unknown proteins, using cellular ATP; since the specificity of such products is uncertain, their use is excluded in vivo;

antisense oligonucleotides directed against the a subunit of CK2, as described in the US Patent Application US 2002/147163 and in the U.S. Pat. No. 6,455,307. However, the inhibition of CK2 demonstrated in vitro is partial and transient, and requires very high doses of antisense oligonucleotides (several tens or several hundreds μg/mL depending on the sensitivity of the cells);

siRNA, as disclosed in the International Application WO 2005/005632.

However, it remains a need of providing new molecules capable of specifically inhibiting the protein kinase CK2 in an effective manner to overcome for instance the problems of resistance in cancer chemotherapy.

The Inventors have now identified competitive inhibitors of the protein kinase CK2.

The subject-matter of the present invention concerns specific compounds, never disclosed for their use as medicament for inhibiting protein kinase CK2, said compounds being selected from those of formula (I):

in which:
the cycle C is a pyrrole heterocycle or a pyrazine heterocycle, $R_1$=—H or an alkyl radical containing 1 to 6 carbon atoms, $R_1$ being present only when the cycle C is a pyrrole heterocycle, $R_2$=—H, an oxygen atom linked to the cycle D by a double bond, a halogen atom, a 1,2-ethanedioxy group (—O—$CH_2$—$CH_2$—O—), a 1,2-ethanedithio group (—S—$CH_2$—$CH_2$—S—), a phenyl group, a benzyl group, a —OR, —SR, —NHR or —N(R)$_2$ group, wherein R=—H or an alkyl radical containing 1 to 6 carbon atoms, $R_3$ being present only when $R_2$ is an oxygen atom linked to the cycle D by a double bond, a 1,2-ethanedioxy group or a 1,2-ethanedithio group, and represents a hydrogen atom or an alkyl radical containing 1 to 6 carbon atoms, $R_4$ and $R_5$, being the same or different, represent a hydrogen atom, an alkyl radical containing 1 to 6 carbon atoms, or a substituted or unsubstituted aryl cycle fused with the cycle D via the carbon atoms 3 and 4, $R_6$ and $R_7$ represent hydrogen atoms, or an aryl cycle fused with the cycle B via the carbon atoms 6 and 7, said aryl cycle being substituted by at least one —OH or —NHR' group, wherein R'=—H or an alkyl radical containing 1 to 6 carbon atoms, $R_8$ and $R_9$ represent hydrogen atoms, or an aryl cycle fused with the cycle B via the carbon atoms 8 and 9, said aryl cycle being substituted by at least one —OH or —NHR' group, wherein R'=—H or an alkyl radical containing 1 to 6 carbon atoms, and with the proviso that:

when $R_6$ and $R_7$ represent an aryl cycle substituted by at least one —OH or —NHR' group, $R_8$ and $R_9$ are hydrogen atoms, and when $R_8$ and $R_9$ represent an aryl cycle substituted by at least one —OH or —NHR' group, $R_6$ and $R_7$ are hydrogen atoms, and their tautomeric forms and their pharmaceutically-acceptable salts for use as a medicament.

The term "alkyl" refers to a straight-chain, or branched alkyl group having 1 to 6 carbon atoms, such as methyl, ethyl, propyl, isopropyl, butyl, isobutyl, sec-butyl, tert-butyl, pentyl, isopentyl, neopentyl, 1-ethyl-propyl, 3-methylpentyl, 2,2-dimethylbutyl, 2,3-dimethylbutyl and hexyl.

The term "aryl" refers to a monocyclic hydrocarbon aromatic or heteroatomic ring system having 6 to 10 ring carbon atoms.

As used herein, the term "halogen" means a halogen atom selected from —F, —Cl, —Br and —I, preferably from —Cl, —Br and —I, and more preferably —Cl.

The expression "pharmaceutically-acceptable" refers to compounds, materials, compositions and/or dosage forms which are suitable for contact with the tissues of human beings and animals without excessive toxicity, irritation, allergic response, or other complications commensurate with a reasonable benefit/risk ratio.

Compounds showing similar structures to those of the present invention have been previously described. In particular, EP 0 402 232 described pyridobenzoindole derivatives, and their additional salts with acids, of general formula:

these compounds being useful as antitumor agents.

Amongst them, compound wherein $R_1$=—H, $R_2$=—OH, $R_3$=—CH$_3$, alk=—(CH$_2$)$_3$— and R=—CH$_3$, named RP60475 or intoplicine, has been extensively studied. This compound is a DNA topoisomerase I and II inhibitor and it demonstrates a strong DNA binding affinity; in vitro, it was found cytotoxic against various cell types with greater cytotoxicity towards solid timorous cells (Bissery et al., Investigational New Drugs, 1993, 11, 263-277; Nabiev et al., Biochemistry, 1994, 33, 9013-9023; Riou et al., Cancer Research, 1993, 53, 5987-5993).

Nguyen et al. have synthesized similar compounds in which the pyrrole heterocycle has been replaced by a pyrazine heterocycle (Nguyen et al., Anticancer Drug Design, 1995, 10, 277-297). In particular, the compounds of formula:

wherein R=—H or —CH$_3$, alk=—(CH$_2$)$_2$— or —(CH$_2$)$_3$— and R'=—CH$_3$ or —C$_2$H$_5$ are strong DNA topoisomerase I and II inhibitors and present antitumoral properties.

This article also describes compounds of formula:

wherein R=—OH or —OCH$_3$, these compounds having no antitumoral activity; this demonstrates that even minor change in the chemical structure of these compounds may lead to different biological activity.

Surprisingly, compounds of formula (I) have been found to be selective inhibitors of protein kinase CK2 without being topoisomerase inhibitors; these compounds have thus been found useful in the development of prevention and/or treatment of pathologies involving CK2 deregulation.

In a preferred embodiment, the cycle C of the compounds of formula (I) of the invention is a pyrrole heterocycle defining a formula (Ia), as follows:

(Ia)

wherein the radicals $R_1$, $R_2$, $R_3$, $R_4$, $R_5$, $R_6$, $R_7$, $R_8$ and $R_9$ are as defined above, the radical $R_1$ being preferably a hydrogen atom.

In another preferred embodiment, the cycle C of the compounds of formula (I) of the invention is a pyrazine heterocycle defining a formula (Ib), as follows:

wherein the radicals $R_2$, $R_3$, $R_4$, $R_5$, $R_6$, $R_7$, $R_8$ and $R_9$ are as defined above.

Preferably, when $R_6$ and $R_7$ or $R_8$ and $R_9$ represent a substituted aryl group, said substituted aryl group is a phenyl cycle substituted by a —OH group.

In another preferred embodiment, the radical $R_2$ is a halogen atom, and more preferably a chlorine atom.

According to another preferred embodiment, the compounds of formula (I) in which the radical $R_4$ is a hydrogen atom and/or the radical $R_5$ is a methyl group are of particular interest because of their very good activity.

According to another particularly preferred embodiment, the radicals $R_4$ and $R_5$ represent a substituted or unsubstituted phenyl cycle fused with the cycle D via the carbon atoms 3 and 4, said compounds of formula (I) responding to the following formula (Ic):

wherein the radicals $R_1$, $R_2$, $R_3$, $R_6$, $R_7$, $R_8$ and $R_9$ are as defined above.

The most preferred compounds of formula (I) according to the invention are the following:

Compound 1:

Compound 2:

As pharmaceutically-acceptable salts there may be mentioned additional salts with inorganic acids such as hydrochlorides, hydrobromides, sulphates, nitrates, phosphates, or with organic acids such as acetate, propionates, succinates, maleates, fumarates, methanesulphonates, p-toluenesulphonates, or substitutes derivatives of these acids.

The compounds of the present invention may be prepared in a number of ways well known to those skilled in the art. The reagents and starting materials are commercially available, or readily synthesized by well-known techniques.

The syntheses of the compounds of the invention are described in the literature:

the synthesis of the compounds of formula (Ia) is described in the following articles: C. H. Nguyen, J-M. Lhoste, F. Lavelle, M. C. Bissery and E. Bisagni, J. Med. Chem., 1990, 33, 1519-1528; C. H. Nguyen, F. Lavelle, J. F. Riou, M. C. Bissery, C. Huel and E. Bisagni, Anti-Cancer Drug Design, 1992, 7, 235-251; and S. Vinogradov, V. Roig, Z. Sergueeva, C. H. Nguyen, P. Arimondo, N. T. Thuong, E. Bisagni, J-S. Sun, C. Hélène and U. Asseline, Bioconjugate Chem., 2003, 14, 120-135;

the synthesis of the compounds of formula (Ib) is described in C. H. Nguyen, E. Fan, J. F. Riou, M. C. Bissery, P. Vrignaud, F. Lavelle and E. Bisagni, Anti-Cancer Drug Design, 1995, 10, 277-297, the synthesis of the compounds of formula (Ic) is described in C. Escudé, C. H. Nuyen, S. Kukredi, Y. Janin, J-S. Sun, E. Bisagni, T. Garestier and C. Hélène, Proc. Natl. Acad. Sci., 1998, 95, 3591-3596.

Usually, reactions are carried out in a suitable solvent. A variety of solvents may be used, provided that it has no adverse effect on the reaction or on the reagents involved. Examples of suitable solvents include: hydrocarbons, which may be aromatic, aliphatic or cycloaliphatic hydrocarbons, such as hexane, cyclohexane, benzene, toluene and xylene; amides, such as dimethylformamide; alcohols such as ethanol, 2-methoxyethanol and methanol; ethers, such as diethylether, diphenylether, tetrahydrofuran, dioxane; acetonitrile; and water.

The reaction can take place over a wide range of temperatures. In general, it is convenient to carry out the reaction at a temperature of from 0° C. to 150° C., and more preferably from about room temperature to 260° C. The time required for the reaction may also vary widely, depending on many factors, notably the reaction temperature and the nature of the reagents. However, provided that the reaction is effected under the preferred conditions outlined above, a period of from 3 hours to 72 hours will usually be sufficient.

The compounds of formula (I) prepared may be recovered from the reaction mixture by conventional means. For example, the compounds may be recovered by distilling off the solvent from the reaction mixture or, if necessary, after distilling off the solvent from the reaction mixture, pouring the residue into water followed by extraction with a water-immiscible organic solvent and distilling off the solvent from the extract. Additionally, the product can, if desired, be further purified by various well-known techniques, such as recrystallisation, reprecipitation or the various chromatography techniques, notably column chromatography or preparative thin layer chromatography.

The Compounds 1 and 2 of the present invention can be obtained according to a process comprising the following steps:

7

II + I

VII

III

VIII

Diphenyl ether
259° C., 40 min.

IV

IX

10% Pd/C, diphenyl
ether 259° C., 45 min.

V

X

POCl₃, BnEt₃NCl,
NEt₂C₆H₅, CH₃CN,
82° C., 10h.

VI

XI

BnEt₃NCl, 12N HCl,
120° C., 72h

Compound 1

Compound 2

The process for the preparation of Compounds 1 or 2 comprises the following key steps:
(i) the condensation of compounds I and II, or I and VII, to obtain a compound III or VIII,
(ii) the indolization by a thermal Fischer indolization of the resulting hydrazone III or VIII, to obtain a compound IV or IX, and
(iii) the aromatization of a compound IV or IX, in the presence of palladium on charcoal, leading directly to a compound V or X.

The indolization step (ii) and the aromatization step (iii) can be performed in the same vessel, each step being controlled to ensure proper completion. The Compound 1 or 2 of the invention is then obtained by boiling the compound V or X in an acetonitrile-phosphorus oxychloride-benzyltriethylammonium chloride-diethylaniline mixture, followed by boiling the methoxy compound VI or XI in a hydrogen chloride aqueous solution and in presence of benzyltriethylammonium chloride.

The present invention also relates to a pharmaceutical composition comprising a compound of formula (I) as defined here-above together with a pharmaceutically-acceptable vehicle or carrier.

The expression "pharmaceutically-acceptable vehicle" refers to any diluents, adjuvants or vehicles, such as preserving agents, fillers, disintegrating agents, wetting agents, emulsifying agents, suspending agents, solvents, dispersion media, coatings, antibacterial and antifungal agents, isotonic and absorption delaying agents and the like.

The biological activities of inhibition of protein kinase CK2 of the compounds of formula (I) have been evaluated (see Examples 2 to 6).

These properties make said compounds as well as their salts suitable as active agent such as antitumor agent, anti-infectious agent, anti-inflammatory agent, anti-malarial agent and agent useful against diabetes, autoimmune and inflammatory diseases and also for use as medicaments in the prevention and/or treatment of disorders and/or diseases related to an excessive activity of CK2 enzyme, in particular for the treatment of mammals, such as human.

Disorders and/or diseases related to an excessive activity of CK2 enzyme are, for example, cancers, in particular breast cancer, prostate cancer, lung cancer, neck and brain cancers, kidney cancer, acute myeloid leukemia, colorectal carcinoma and pancreatic cancer; autoimmune and inflammatory diseases, for example, glomerulonephritis; infectious diseases, such as viruses infections, for example, HIV, CMV, HPV, PV, Herpes Simplex Virus 1 (HSV-1), Hepatitis C Virus (HCV), Influenza virus, etc.; diabetes; angiogenesis related disorders; retinopathies (such as age related macular degeneration, ARMD) and cardiac hypertrophy.

The amount of compound of formula (I) to be administered to humans, or optionally to animals, depends on the specific activity of this compound, which activity can be measured by means which will be disclosed in the following examples. It also depends on the severity of the illness to be treated, and on the age and the weight of the individual.

In addition to the above provisions, the invention also comprises other provisions which will become clear from the description which follows, which refers to examples illustrating the biological activity of compounds of general formula (I), and also to the attached drawings in which.

EXAMPLE 1

Synthesis of the Compounds of Formula (I)

The Compounds 1 and 2 of formula (I) were synthesised according to the procedure described and published in Bioconjugate Chem., 2003, 14, 120-135.

EXAMPLE 2

Characterization of the CK2 Inhibitory Activity of Compounds of Formula (I)

In order to characterize the mode of action of compounds of formula (I), they have been tested on CK2, c-kit and topoisomerase II activity and on their DNA intercalation capacity.
1. Materials and Methods
Effect of compounds of formula (I) on CK2 activity is measured according to Prudent et al. (Prudent, R. et al. (2008) Mol Cell Biochem 316(1-2): 71-85): compounds were tested in a radioactive assay performed in a final volume of 18 μL containing 3 μL of compounds at the indicated concentrations, 3 μL, of CK2α (36 ng) and a mixture containing 100 μM of peptide substrate (RRRE-DEESDDEE, SEQ ID No: 1), 10 mM MgCl$_2$, and 100 μM [γ-$^{32}$P]-ATP. Assays were performed at room temperature for 5 min before termination by the addition of 60 μL of 4% TCA. $^{32}$P incorporation into the peptide substrate was determined as previously described in Filhol et al. (Biochemistry 29: 9928-36, 1990).

Effect of compounds of formula (I) on c-kit activity is measured according to the manufacturer's recommendations (Millipore, reference 14-559): in a final reaction volume of 25 μL, c-Kit (5-10 mU) is incubated with 8 mM MOPS pH 7.0, 0.2 mM EDTA, 10 mM MnCl$_2$, 25 μM ATP, 0.1 mg/mL poly(Glu, Tyr) 4:1, 10 mM MgAcetate and [γ-33P-ATP] (specific activity approx. 500 cpm/pmol, concentration as required). The reaction is initiated by the addition of the MgATP mix. After incubation for 40 minutes at room temperature, the reaction is stopped by the addition of 5 μL of a 3% phosphoric acid solution. 10 μL of the reaction is then spotted onto a Filtermat A and washed three times for 5 minutes in 75 mM phosphoric acid and once in methanol prior to drying and scintillation counting.

Effect of compounds of formula (I) on topoisomerase II activity is measured according to the manufacturer's recommendations (Vaxron, TA-001): in a final reaction volume of 10 μL, 1U topoisomerase IIα is incubated with 0.1M Tris-HCl, pH 8.0, 2 mM DTT, 20 mM MgCl$_2$, 4 mM ATP, 0.2 M NaCl, 2 μg BSA, 500 ng Kinetoplast DNA and compounds to be assayed (from 10 mM stock solution in DMSO, final concentration of DMSO<1%). The reaction is initiated by the addition of topoisomerase IIα. After incubation for 15 min at 37° C., reaction is stopped by addition of 1 μL of stop solution (3% SDS, 1.5 mg·mL$^{-1}$ Proteinase K). Following an incubation of 30 minutes at 37° C., reaction mixture is resolved on an agarose gel (1% agarose) and DNA topoisomers are quantified by densitometric analysis.

Effect of compounds of formula (I) on DNA intercalation. DNA intercalation was performed using FID (Fluorescence Intercalator Displacement). This assay based on the loss of fluorescence of a DNA-bound intercalator (thiazole orange) upon displacement by a DNA-binding molecule. Briefly, the double stranded oligonucleotide CAATCGGATCGAATTCGATCCGATTG (SEQ ID No: 2) (0.25 μM) is mixed to thiazole orange (0.75 μM) in a buffer containing cacodylate 10 mM, KCl pH 7.2 100 mM. Tested compounds, as well as ethidium bromide (positive control) are added to the mix (0.75 μM-10 μM). After 20 minutes incubation, fluorescence is measured (excitation: 490 nm, emission: 520 nm). In this assay, compound auto-fluorescence was negative.

2. Results: Activity of Compounds of Formula (I) in Comparison to Two Compounds Out of the Invention The formulae of Compound 3 and Compound 4 respond respectively to the formulae of Compound 1 and Compound 2 of the present invention, in which the —OH group of the aryl cycle is replaced by a —OCH$_3$ group. Compound 4 specifically responds to the definition of a compound disclosed in the prior art: the compound 6 described in Thi My-Nhung Hoang et al., Cell Cycle, 2009, Vol. 8, No. 5, pages 765-772.

TABLE I

Percentage of several enzymatic activity (CK2, c-kit and topoisomerases II) and of DNA intercalation in presence of Compound 1 or 2, and percentage of remaining CK2 activity in presence of Compound 3 or 4

| Compound | % remaining CK2 activity (10 μM) | % remaining c-kit activity (10 μM) | % remaining topoisomerase II activity (10 μM) | % DNA intercalation (10 μM) |
| --- | --- | --- | --- | --- |
| 1 | 1.4 (IC$_{50}$ = 1.5 μM) | 60.4 | 106.8 | 62.0 |
| 2 | 3.5 (IC$_{50}$ = 0.67 μM) | 16.9 | 77 | 66.4 |
| 3 | 94.0 | — | — | — |
| 4 | 73.0 | — | — | — |

These results show that Compounds 1 and 2 strongly inhibit CK2 activity, i.e. the remaining CK2 activity is very low for these two compounds, in comparison to Compounds 3 and 4, but have no or few inhibitory effect on c-kit and topoisomerase II activity or on DNA intercalation; Compounds of formula (I) are selective inhibitors of protein kinase CK2.

EXAMPLE 3

Cell-Potent CK2 Inhibitory Activity of Compounds of Formula (I)

1. Materials and Methods

A cellular assay has been developed to test the inhibition potential of compounds towards CK2, into living cells.

Cellular CK2 activity assay: The plasmid pEYFPc1 expressing a chimeric YFP-based CK2 activity reporter was designed by adding six CK2 consensus phosphorylation sites at the C terminus of the YFP protein (pEYFPc1-SβS). pEYFPc1-SβS was obtained from pEYFPc1-CK2β after two subsequent rounds of mutations with the Quickchange-Site Directed mutagenesis kit (Stratagene) using for mutagenesis 1:

```
                                          (SEQ ID No: 3)
5'-GCTCAAGCTTCGGATTCTGAAGACGACGATACCGCGGGCCCG-3'
and
                                          (SEQ ID No: 4)
5'-CGGGCCCGCGGTATCGTCGTCTTCAGAATCCGAAGCTTGAGC-3'
and
for mutagenesis 2:
                                          (SEQ ID No: 5)
5'-GCTCTGAGGAGGTGTCCGAGGTCGACTGGTTCTGAGGGCTCCGT-3'
and
                                          (SEQ ID No: 6)
5'-CGGGCCCGCGGTATCGTCGTCTTCAGAATCCGAAGCTTGAGC-3'
(Prudent et al., Biochim Biophys Acta. 2008;
1780(12):1412-20).
``` transfection of HeLa cells with the plasmid,

HeLa cells were plated at 10$^6$ cells/well in 12 well plates and transfected with the CK2 activity reporter plasmid (pEYFPc1-SβS) using the lipofectamine reagent (Invitrogen).

test of CK2 inhibitory activity: as a positive control, TBB inhibition of CK2 activity in living cells is first tested: HeLa cells transfected with the plasmid expressing a chimeric CK2 activity-GFP-based reporter are incubated for 24 hours with the CK2 inhibitor TBB, and with DMSO as a negative control.

Cells extracts are then analyzed by native electrophoresis, and GFP (Green Fluorescent Protein) is revealed by immunoblotting: one day after transfection, the culture medium was replaced with fresh medium containing the compounds and incubated for 24 hours. Then, the cells were collected and the washed pellets were solubilized for 30 mM in ice with 100μA of lysis buffer (Tris 50 mM pH=7.4, 0.15 M NaCl, EDTA 2 mM, Triton X100 1/100, phosphatase inhibitor cocktail 2 (Sigma) 1/100, and leupeptine, aprotinine, AEBSF according to the manufacturer recommendations). 50 μg of proteins were loaded with a mix of glycerol and bromophenol blue and migrated through a 12% native-polyacrylamide gel. After electro-transfert, the nitrocellulose membrane was blocked with BSA 1% and incubated overnight at 4° C. with the mAb anti-GFP (Roche, ref. 1814460) at 1/1000. After washings, the membrane was incubated with a goat anti-mouse-HRP secondary antibody (Sigma, ref. A4416) at 1/2000 for 1 hour and GFP was revealed with the ECL plus western blotting detection system (GE Healthcare).

Several concentrations of Compounds 1 and 2 are tested in the same conditions in the cellular CK2 activity assay.

2. Results

Figure 2:
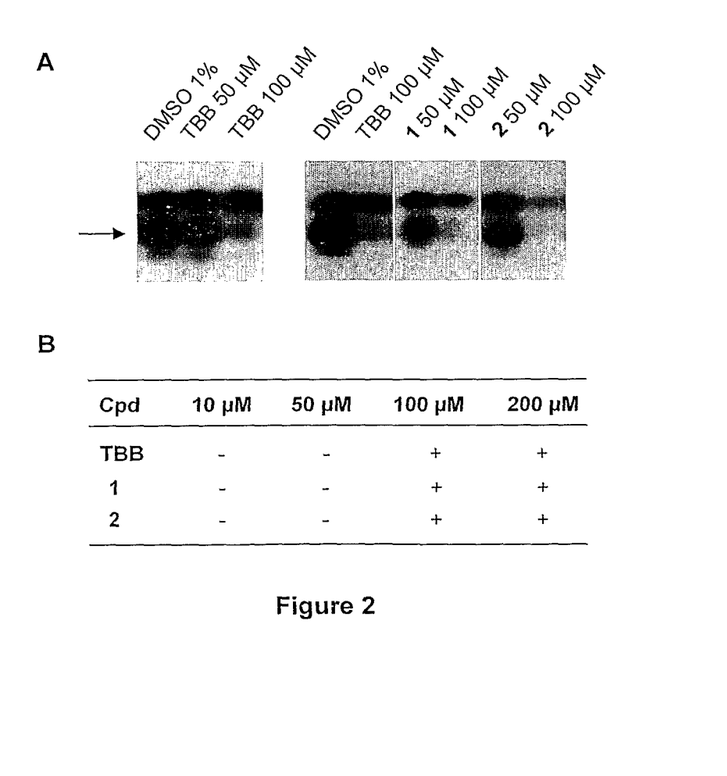
FIGS. 2A and 2B show the inhibition of CK2 activity by TBB, Compounds 1 and 2 in living cells.

In non-treated or DMSO-treated HeLa cells, CK2 is fully active and the CK2 activity reporter could be found mostly as a phosphorylated isoform (see lower band on FIG. 2A).

When cells are incubated 24 hours either with the known CK2 inhibitor TBB, Compound 1 or Compound 2, the phosphorylated CK2 reporter isoform disappeared in a dose-dependent manner due to specific CK2 activity inhibition (see FIGS. 2A and 2B).

Table II below shows activity of TBB, Compounds 1 and 2 in the cellular CK2 activity assay:

TABLE II

Dose-dependent activity of Compounds 1 and 2 in the cellular CK2 activity assay

| Compound | 10 μM | 50 μM | 100 μM | 200 μM |
|---|---|---|---|---|
| TBB |  |  | + | + |
| 1 | − | − | + | + |
| 2 | − | − | + | + |

These results confirm that Compounds 1 and 2 inhibit CK2 activity into cells.

EXAMPLE 4

Characterisation of Inhibition of Cell Proliferation by Compound 1 and Compound 2

As known CK2 inhibitors decrease cell viability, viability of several cell types has been measured after 48 hours treatment with Compounds 1 and 2.

1. Materials and Methods

Cells: HeLa (human cervical adenocarcinome) and U373 (human glioblastoma) cancer cell lines, The inhibition of HeLa cell proliferation is assessed as follows: HeLa cells were plated into 96-well plates at $1.5 \times 10^4$ cells/well. The following day, the culture medium was replaced with fresh medium (Dulbecco's medium, Invitrogen Life Technologies, Inc., supplemented with 10% (v/v) fetal calf serum (FBS, BioWest)), containing increasing concentration of inhibitors or an equivalent amount of DMSO as control. Two days later, cell viability was measured with the CellTiter-Glo® Luminescent Cell Viability Assay (Promega) according to the manufacturer recommendations.

The inhibition of U373 cells proliferation is assessed with the same protocol that HeLa cells: one day after plating, U373 cells are treated with 5 μM of Compound 1, Compound 2 or DMSO. Results are given relative to the luminescence recorded for DMSO.

2. Results

Figure 3:
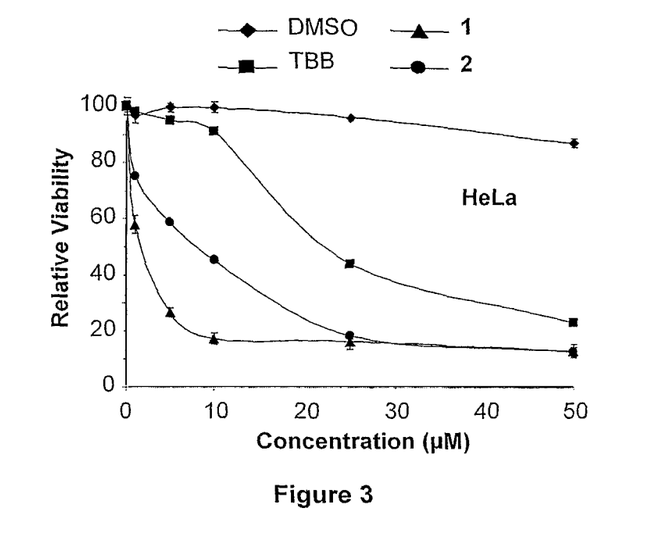
FIG. 3 is a graph of relative viability vs concentration (μM) of tested compounds showing the inhibition of HeLa cell proliferation by Compounds 1 and 2 compared to DMSO and TBB.

Decrease of Cell Viability of HeLa Cells:

Compounds 1 and 2 induce a strong inhibition of tumour cell proliferation even at low doses (FIG. 3).

Figure 4:
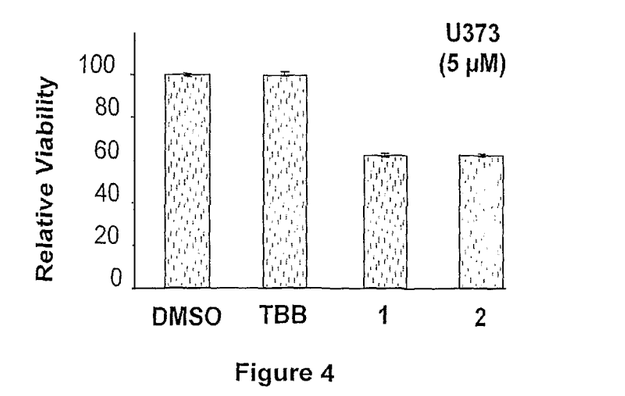
FIG. 4 shows the inhibition of U373 cancer cells proliferation by Compounds 1 and 2 compared to DMSO and TBB.

Decrease of Cell Viability of U373 Cancer Cell Lines:

5 μM of Compound 1 and of Compound 2 are potent to reduce cell proliferation of these cell lines after 48 hours treatment (FIG. 4).

EXAMPLE 5

Analysis of Cell Cycle Inhibition by Compound 1

1. Materials and Methods

Cells previously treated with Compound 1 and Compound 2 in example 4 are then submitted to a cell cycle analysis following propidium iodide incorporation.

Cell cycle distribution analysis: cells were plated in 6-well plates. The following day, cells were treated with 5 μM compounds or an equivalent amount of DMSO. After 24 hours, cells were harvested, fixed with ethanol 70% for 30 minutes, and labeled with propidium iodide 10 μg/mL for 30 min. DNA content was analysed with FACScalibur and Cell Quest software.

2. Results

Figure 5:
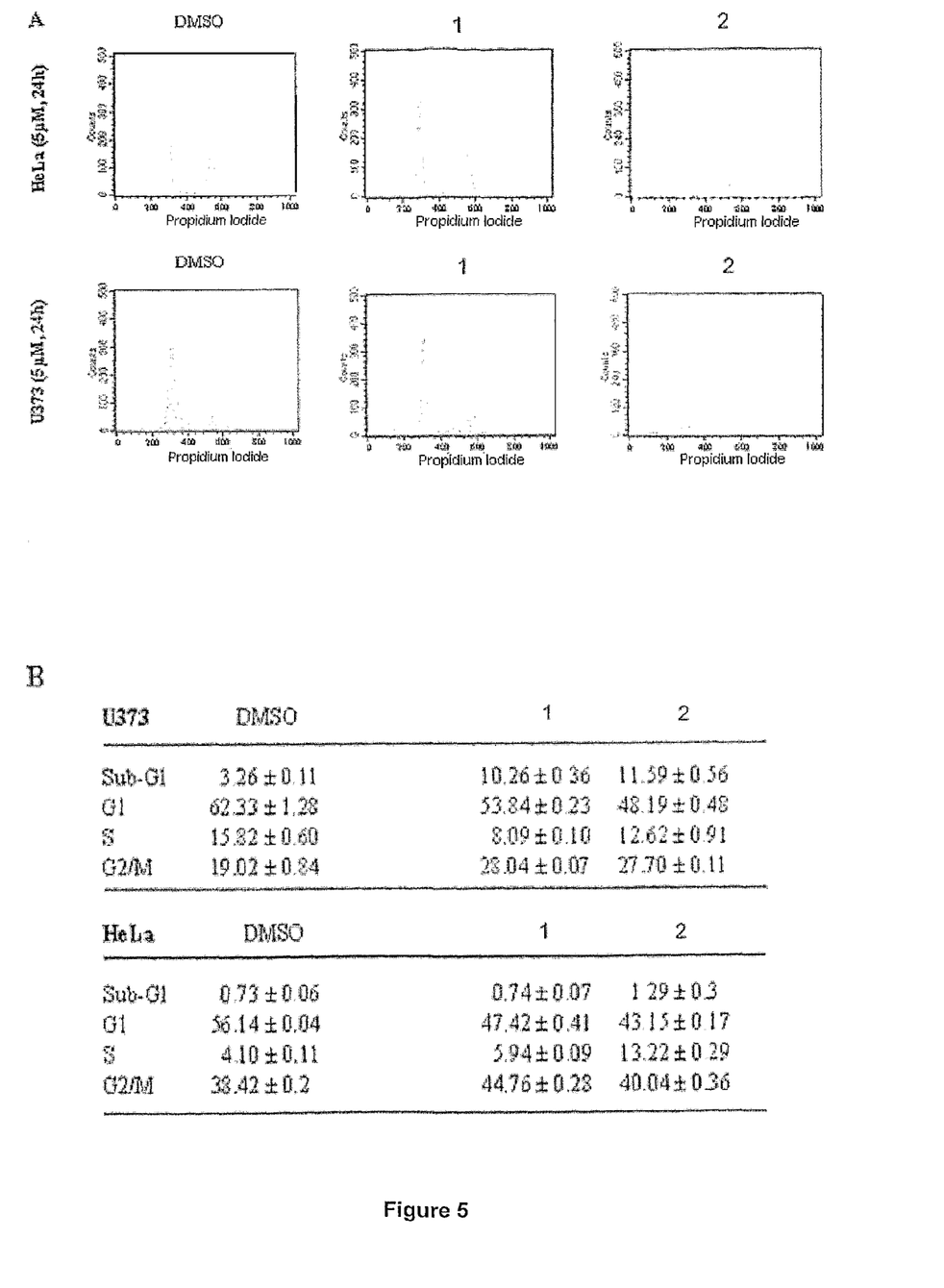
FIGS. 5A and 5B illustrate the analysis of the influence of Compound 1 and Compound 2 on the cellular cycle in HeLa (p53 positive) wild cell types and in U373 cells (p53 negative).

Analysis showed that HeLa and U373 cells treated with Compound 1 and Compound 2 exhibited a cell cycle arrest with a substantial accumulation in G2/M-phase, and a concomitant increase of apoptotic cells in HeLa-treated cells is also observed, this is not observed in U3763 cells, these cells being resistant to apoptosis (FIG. 5A). The proportion (%) of HeLa and U373 cells in sub-G1, G1, S and G2/M phases are summarized in the table of FIG. 5B.

EXAMPLE 6

Inhibition of Tumorigenesis in Tumor Cells by Compound 1

1. Materials and Methods

The effect of compound on tumor cell tumorigenesis is tested on a colony formation assay.

The inhibition of colony formation assay by soft agar culture is performed as follows: U373 cells were poured on a 0.6% agar-DMEM-10% FBS layer, imbedded in 0.3% agar-DMEM-10% FBS, containing compounds (5 μM) or equivalent amount of DMSO. Number of colonies (more than 20 cells) was counted 15 days later in 10 fields/well. Experiment was done in duplicate at least twice.

2. Results

Figure 6:
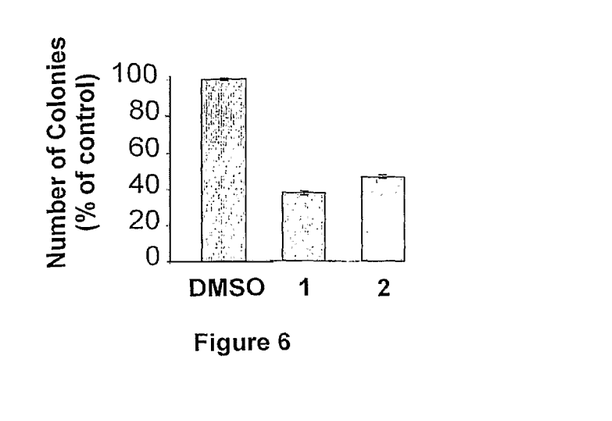
FIG. 6 shows inhibition of cell colony formation on soft agar medium by Compounds 1 and 2 compared to DMSO.

As shown in FIG. 6, 5 μM of Compound 1 are enough to induce 50% of inhibition of colony formation.

EXAMPLE 7

In Vivo Inhibition of Tumorigenesis by Compound 1

1. Materials and Methods

All experimental procedures adhered to local ethical committee (Comité régional d'éthique pour l'Expérimentation animale CREEA, Rhône Alpes—protocol n°286). Female Harlan athymic nude mice (6-8 weeks) were inoculated s.c. into the right flank with $7.5 \times 10^5$ U373 cells. When tumors reaches±50 mm³ (volume=length×width×height), animals were treated i.p. 3 times weekly (every two days) for 2 weeks, with Compound 1 (0.14 mg/100 μL/injection-4 mice) dissolved in PEG3350 22.5%, BSA 0.45% or equivalent DMSO (10% final-3 mice) dissolved in same buffer (control group). Body weight and tumor volume were determined twice weekly. The experiment was terminated when tumor volume was about 1000 mm³. Results are presented as mean±standard error of the mean (SEM).

2. Results

Figure 7:
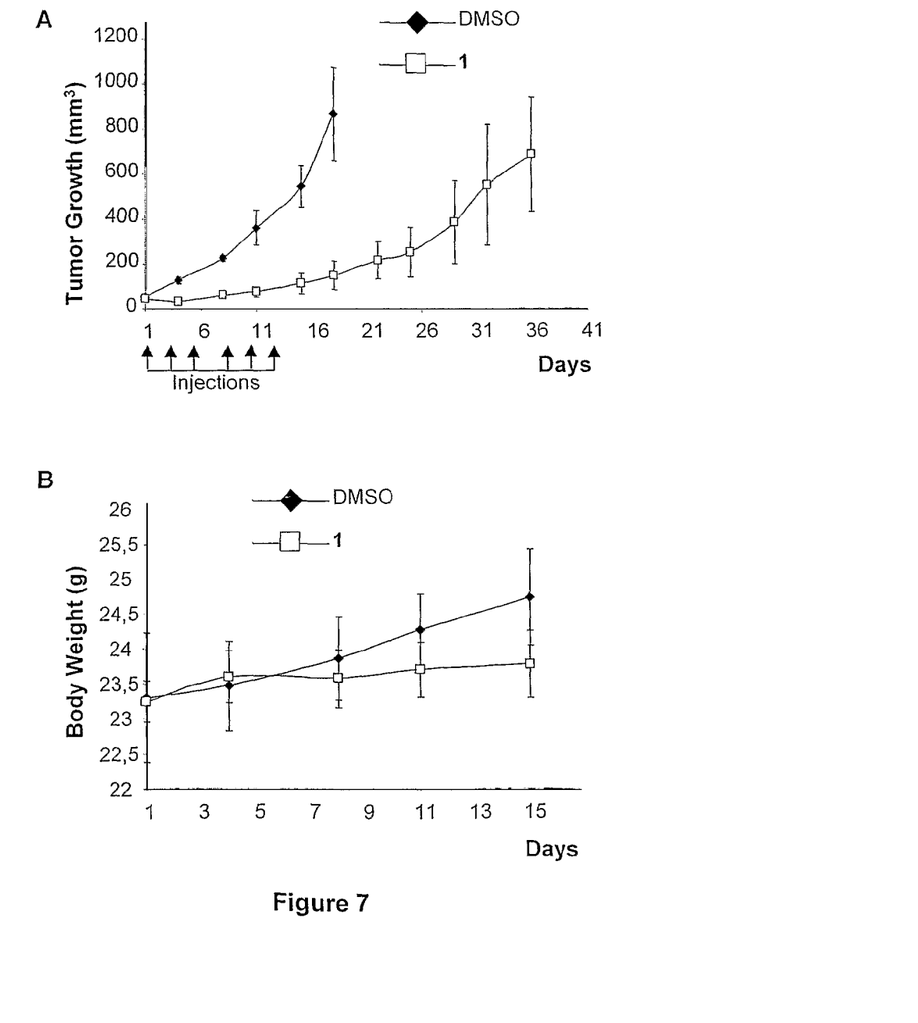
FIG. 7A is a graph (Tumor Growth (mm$^3$) vs time (days)) showing the in vivo inhibition of tumour growth induced by Compound 1 compared to DMSO.
FIG. 7B is a graph (Body weight (g) vs time (days)) showing the variation of body weight during this study.

It is observed that tumor incidence was significantly reduced across all time points in mice injected with Compound 1 compared to those injected with DMSO (FIG. 7A). By 15 days post first compound injection, mice injected with Compound 1 had tumors that were 4.7 times smaller than those injected with DMSO. Furthermore, the recorded variations in body weight were not statistically significant showing that Compound 1 was well tolerated at the doses applied (FIG. 7B).

EXAMPLE 8

Structure-Activity Relationship Study

Structure-activity relationships also indicate that some positions are tolerant for substitution. The X-Ray co-structure of the complex CK2-compound of formula (I) gives us deeper insights into the molecular interaction between the kinase and the inhibitor.

X-Ray Co-Structure of the Complex CK2-Compound of Formula (I):

In the X-Ray structure of the complex CK2-compound of formula (I), it can be observed that a hydrogen bonding is established between the —OH group of the phenyl cycle of Compound (I) and the nitrogen backbone of Val116, providing a rational for the need of a free —OH group at this position.

Concerning the radical $R_3$, it appears that when it is exposed to a solvent its activity is reduced due to the unfavourable hydrophobic interactions of the radical $R_3$ with water. This is consistent with the highly solvent-exposed environment of the position of the radical $R_3$.

The invention claimed is:

1. A medicament, comprising:
a compound of formula (I):

(I)

a tautomeric form of the compound of formula (I), a pharmaceutically acceptable salt of the compound of formula (I), or a combination thereof,
wherein C is a pyrrole heterocycle or a pyrazine heterocycle,
$R_1$ is H or an alkyl radical comprising from 1 to 6 carbon atoms, $R_1$ being present only when C is a pyrrole heterocycle,
$R_2$ is H, an oxygen atom double bonded to D, a halogen atom, a 1,2-ethanedioxy group, a 1,2-ethanedithio group, a phenyl group, a benzyl group, —OR, —SR, —NHR, or —N(R)$_2$, R is H or an alkyl radical comprising from 1 to 6 carbon atoms,
$R_3$ is present only when $R_2$ is an oxygen atom double bonded to D, a 1,2-ethanedioxy group, or a 1,2-ethanedithio group,
if $R_3$ is present, it is a hydrogen atom or an alkyl radical comprising from 1 to 6 carbon atoms,
$R_4$ and $R_5$ are each independently a hydrogen atom or an alkyl radical comprising from 1 to 6 carbon atoms, or together are a substituted or unsubstituted aryl cycle fused with D via carbon atoms 3 and 4,
$R_6$ and $R_7$ are both hydrogen atoms, or together are an aryl cycle substituted by an —OH group, an —NHR' group, or both, wherein R' is H or an alkyl radical comprising from 1 to 6 carbon atoms,
$R_8$ and $R_9$ are both hydrogen atoms, or together are an aryl cycle substituted by an —OH group, an —NHR' group, or both, wherein R' is H or an alkyl radical comprising from 1 to 6 carbon atoms, and
with the proviso that either $R_6$ and $R_7$ or $R_8$ and $R_9$ together is an aryl cycle substituted by —OH or —NHR' or both, R' is H or an alkyl radical comprising from 1 to 6 carbon atoms,
wherein if $R_6$ and $R_7$ is an aryl cycle then the aryl cycle is fused with B via carbon atoms 6 and 7, and $R_8$ and $R_9$ are hydrogen atoms, and
if $R_8$ and $R_9$ together is an aryl cycle then the aryl cycle of $R_8$ and $R_9$ is fused with B via carbon atoms 8 and 9, and $R_6$ and $R_7$ are hydrogen atoms; and
a pharmaceutically acceptable excipient or carrier.

2. The medicament of claim 1, wherein C is a pyrrole heterocycle and $R_1$ is a hydrogen atom.

3. The medicament of claim 1, wherein $R_6$ and $R_7$ together are an aryl cycle, which is substituted by an —OH group and is fused with B via carbon atoms 6 and 7.

4. The medicament of claim 1, wherein $R_8$ and $R_9$ together are an aryl cycle, which is substituted by an —OH group and is fused with B via carbon atoms 8 and 9.

5. The medicament of claim 1, wherein $R_2$ is a halogen atom.

6. The medicament of claim 5, wherein $R_2$ is a chlorine atom.

7. The medicament of claim 1, wherein $R_4$ is a hydrogen atom.

8. The medicament of claim 1, wherein $R_5$ is a methyl group.

9. The medicament of claim 1, wherein $R_4$ and $R_5$ together are a substituted or unsubstituted phenyl cycle fused with D via carbon atoms 3 and 4, said compounds of formula (I) responding to the following formula (Ic):

(Ic)

10. The medicament of claim 1, comprising a compound of formula:

formula:

or both.

11. The medicament of claim 1, wherein C is a pyrazine heterocycle.

12. The medicament of claim 3, wherein $R_6$ and $R_7$ together are a phenyl cycle.

13. The medicament of claim 4, wherein $R_8$ and $R_9$ together are a phenyl cycle.

14. The medicament of claim 1, comprising a pharmaceutically acceptable salt of a compound of formula (I), wherein the pharmaceutically acceptable salt is a hydrochloride, a hydrobromide, a sulphate, a nitrate, a phosphate, an acetate, a propionate, a succinate, a maleate, a fumarate, a methanesulphonate, a p-toluenesulphonate, or a mixture thereof.

* * * * *

UNITED STATES PATENT AND TRADEMARK OFFICE
CERTIFICATE OF CORRECTION

PATENT NO.       : 8,686,144 B2
APPLICATION NO.  : 13/387912
DATED            : April 1, 2014
INVENTOR(S)      : Claude Cochet et al.

It is certified that error appears in the above-identified patent and that said Letters Patent is hereby corrected as shown below:

On the title page, Item (73), should read:

-- (73) Assignees:   Commissariat a l'Energie Atomique et aux Energies Alternatives, Paris (FR); Institut National de la Sante et de la Recherche Medicale (INSERM), Paris (FR); Institut Curie, Paris (FR); Centre National de la Recherche Scientifique, Paris (FR)

Signed and Sealed this
Fifteenth Day of July, 2014

Michelle K. Lee
*Deputy Director of the United States Patent and Trademark Office*

SEQUENCE LISTING

```
<160> NUMBER OF SEQ ID NOS: 6

<210> SEQ ID NO 1
<211> LENGTH: 12
<212> TYPE: PRT
<213> ORGANISM: Homo sapiens

<400> SEQUENCE: 1

Arg Arg Arg Glu Asp Glu Glu Ser Asp Asp Glu Glu
1               5                   10

<210> SEQ ID NO 2
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 2
caatcggatc gaattcgatc cgattg                                          26

<210> SEQ ID NO 3
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 3
gctcaagctt cggattctga agacgacgat accgcgggcc cg                        42

<210> SEQ ID NO 4
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 4
cgggcccgcg gtatcgtcgt cttcagaatc cgaagcttga gc                        42
```

-continued

```
<210> SEQ ID NO 5
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 5
gctctgagga ggtgtccgag gtcgactggt tctgagggct ccgt                44

<210> SEQ ID NO 6
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 6
cgggcccgcg gtatcgtcgt cttcagaatc cgaagcttga gc                  42
```